ns of Sunflower (Helianthus annus)", *J. Food Sci.*, 47(1): 40–42 (1982).
P. G. Pifferi and A. Vacarri, "The Anthocyanins of
United States Patent [19]
Mason et al.

[11] Patent Number: 4,888,173
[45] Date of Patent: Dec. 19, 1989

[54] ANTHOCYANIN BIRD REPELLENTS

[75] Inventors: James R. Mason, Philadelphia, Pa.; Michael A. Adams, Haddonfield, N.J.

[73] Assignee: Monell Chemical Senses Center, Philadelphia, Pa.

[21] Appl. No.: 62,219

[22] Filed: Jun. 12, 1987

[51] Int. Cl.$^4$ ..................... A61K 35/78; A61K 31/35
[52] U.S. Cl. ................................. 424/195.1; 514/456; 514/918; 71/23; 71/64.01
[58] Field of Search ..................... 424/195.1; 514/456; 514/918; 71/23, 64.01

[56] References Cited

PUBLICATIONS

Harborne, Jeffrey, "Flavonoid Pigments", Herbivores; Their Interaction with Secondary Plant Metabolites, G. A. Rosenthal and D. H. Janzen (eds.) Academic Press: New York, C. 18, pp. 619–655.
A. Vacarri, P. G. Pifferi and G. Zaccerini, "Anthocyanins of Sunflower (Helianthus annus)", *J. Food Sci.*, 47(1): 40–42 (1982).
P. G. Pifferi and A. Vacarri, "The Anthocyanins of Sunflower II., A Study of the Extraction Process", *J. Fd. Technol.*, (1983) 18, 629–638.
"Contribution of Seed Hull Characteristics to Resistence of Sunflower to Blackbird Damage", J. R. Mason et al, *North Dakota Farm Research Bimonthly Bulletin*, May–Jun., 1986, pp. 16–20.
"Field Trials of Sunflower Resistent to Bird Depredation", R. A. Dolbeer et al. *North Dakota Farm Research Bimonthly Bulletin*, May–Jun. issue, p. 21.

*Primary Examiner*—John W. Rollins
*Attorney, Agent, or Firm*—Woodcock Washburn Kurtz Mackiewecz & Norris

[57] ABSTRACT

Anthocyanins have been found to be taste-aversive to avian species. This invention relates to mammalian livestock feeds and pelleted fertilizer and pesticide compositions each incorporating effective avian-repellent amounts of such anthocyanins or anthocyanin-containing plant materials. The invention also relates to avian-repellent compositions for application to crops and seeds incorporating such anthocyanins.

19 Claims, 1 Drawing Sheet

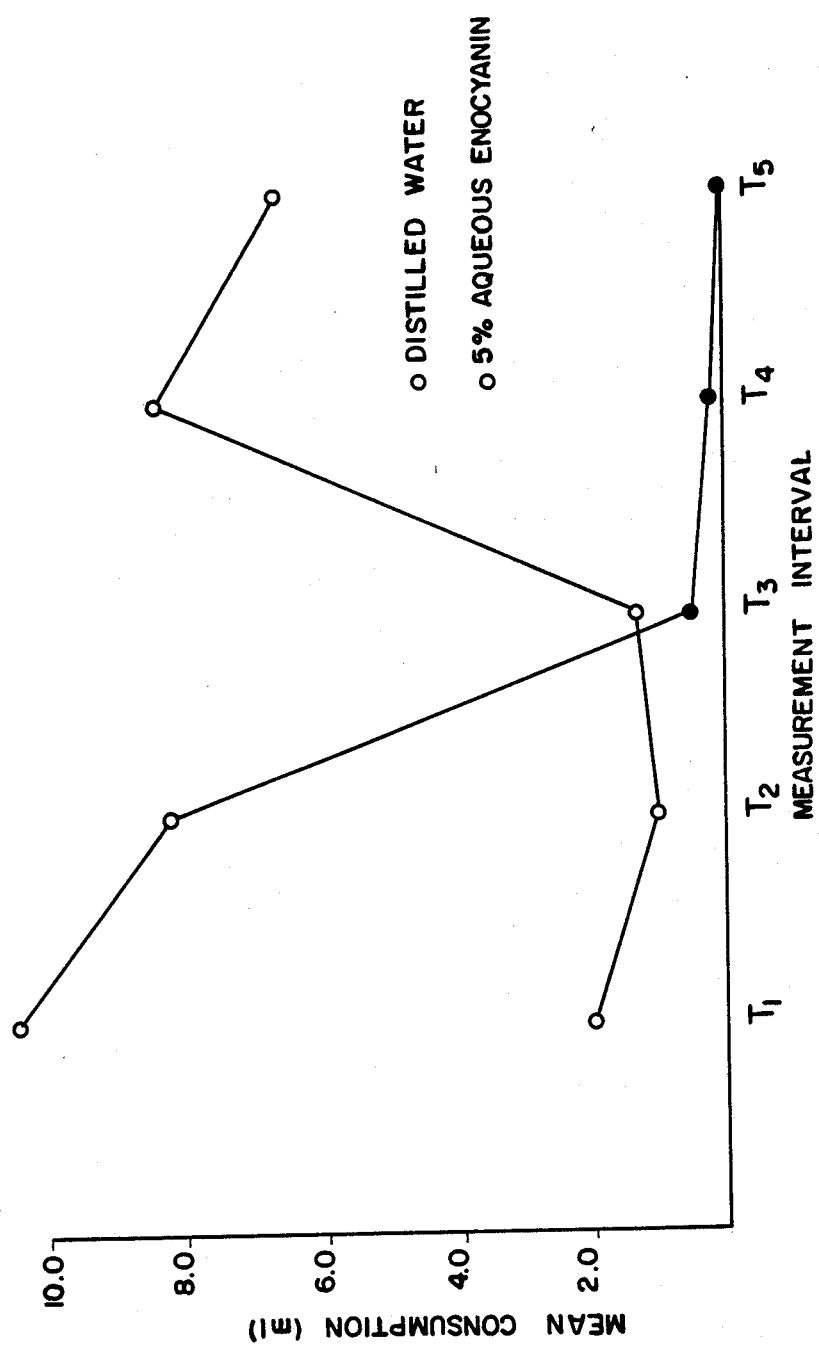

ANTHOCYANIN BIRD REPELLENTS

BACKGROUND OF THE INVENTION

The present invention relates to the field of livestock feeds which include effective amounts of materials which are distasteful to avian species and to avian repellent compositions.

Certain embodiments of the present invention relate to materials and methods for reducing agricultural losses due to avian species, especially many passerine species (e.g., European Starling [*Sturnus vulgaris*]; Red-winged Blackbird [*Agelaius phoeniceus*], American Robin [*Turdus migratorius*], and American Goldfinch [*Carduelis tristis*]). The cost of starling damage, for example, to an individual farmer from consuming livestock feed can vary considerably from negligible loss up to several thousand dollars during the fall-winter damage season. Palmer, T. K. 1976, "Pest Bird Damage Control in Cattle Feedlots: The Integrated Systems Approach", *Proc. Vertebr. Pest Control Conf.* Monterey, Calif. 7:17–21. Generally, the large beef cattle feedlots of the west have the most significant losses. However, moderately sized dairy farms in Tennessee feeding 100 to several hundred head of cattle have been estimated to sustain losses of several hundred dollars during a 3-month damage season. Glahn, J. F., (1983) "Blackbird and Starling Depredations at Tennessee Livestock Farms", *Proc. Ninth Bird Control Seminar,* Bowling Green, Ohio, 125–134. Although starlings can be a problem at hog operations, hog producers need not suffer significant feed loss problems with the use and propr adjustment of flip-top feeders and confinement of swine when feeding. Nevertheless, Tennessee farmers report losses in feedlots of up to 10% due to birds. A similar study in the United Kingdom estimated losses to farmers at up to 12%. Feare, C. J., and K. P. Swannakc, "Starling Damage and its Prevention at an Open-Fronted Calf-Yard," *Anim. Prod.* 26:259–265 (1978).

The distribution and magnitude of feed loss damage on a national scale has not been studied. However, one study in the winter of 1980 inspected 287 livestock farms in six selected livestock producing counties in Tennessee. Glahn, J. F. supra. Results of this study indicated that 26% of the farms had more than a negligible bird damage problem, including 6% with significant problems where losses exceeding $100 per season would be expected. Based on Tennessee Agricultural Statistics there were 43,000 hog and dairy farms in that state in 1980. However, since the bird damage survey only samples farms with more than twenty head of livestock, the authors estimated the sampled population at 25,900 farms. Therefore, the 6% of the farms that could have benefited from control measures was 1,554. These data are subject to seasonal changes in bird populations, weather conditions, and farm practices, but give some idea of the number of farms that might benefit from bird control measures.

Further analysis of the previous data indicated that the primary factors influencing the distribution of damage were: proximity of roosting starlings to the farm; snow cover; mean temperatures below freezing on the day of inspection; and the number of head of livestock consuming feed. Glahn, J. F., and D.K. Otis, "Factors Influencing the Distribution of Bird Depredations at Livestock Feeding Areas in Tennessee," Bird Damage Research Report No. 231, Denver Wildlife Research Center, Denver, Colo. (1982). Since starlings winter throughout much of the United States, varying degrees of damage at farms might be expected depending on winter weather conditions and size of livestock farms, with most serious problems occurring at large farming operations located in the northern wintering range of the starling. Although the total number of livestock farms in the U.S. is not readily determined, it is known that in 1982 Tennessee had 85,000 dairy farms and 23,000 hog farms with 217,000 milk cows and 750,000 hogs compared with national livestock figures of 11 million milk cows and 53 million swine, respectively. The number of beef cattle on feed or the number of major beef cattle feedlots were not readily available.

It is extremely difficult to quantify the costs associated with the spread of disease to livestock by starlings essentially because it is very difficult to document the effects of avian disease transmission. Two studies have implicated starlings in the spread of transmissible gastroenteritis (TGE) to swine, but no known data exist for other livestock diseases. Gough, P. M., and J. W. Beyer, 1982, "Bird-Vectored Diseases," *Proc. Fifth Great Plains Wildlife Damage Control Workshop* (R. M. Timm and R. J. Johnson, Eds.), University of Nebraska, Lincoln Neb. pp. 260–272; and Pilchard, E.J. 1965, "Experimental Transmission of Transmissible Gastroenteritis Virus by Starlings: *J. Vet. Res.* 26(114):1177 1179 The costs of TGE to farmers in terms of stock loss may be substantial. For example, during the winter of 1978–79 a TGE outbreak occurring in southeast Nebraska resulted in the death of 10,000 pigs in one county alone. Because of the possible threat of disease outbreak due to birds, livestock operators and particularly hog producers would be willing to use a material which would keep the birds out of their feedlots. The success of a feed repellent depends both on the effectiveness of the material and the amount of treated feed available to birds.

Few objective estimates of damage by other avian species are available, but in addition to losses from starlings (*Sturnus vulgaris*), depredation from other species such as red-winged blackbirds at swine and cattle feedlots are considered serious. Besser, J. F. W. C. Royall and J. W. Degrazio, "Baiting Starlings with DRC-1339 at a Cattle Feedlot," *J Wildl. Manaqe.*, 31:48–51 (1967); Besser, J. F. J. W. Degrazio and J.L. Guarino, "Costs of Wintering Starlings and Red-Winged Blackbirds at Feedlots," *J Wildl. Manage.* 32:179–180 (1968); Feare, C.J., "Cost of Starling Damage of an Intensive Husbandry Unit," *Proc. British Insecticide and Fungcide Conf.* 8:253–259 (1975); Feare, C.J. (1980), "The Economies of Starling Damage," *Econ. of Dam.* 2:39–54; Stickley, A.R., "Extended Use of Starlicide in Reducing Bird Damage in Southeastern Feedlots,"*Proc. Bird. Cont. Sem.* 8:79–89 (1979); and Twedt, D. J. and J. F. Glahn, "Reducing Starling Depredations at Livestock Feeding Operations Through Changes in Management Practices," *Proc. Vertebr. Pest. Conf.* 10:159–163 (1982). Losses may result from feed contamination and disease transmission or from feed consumption, and problems are exacerbated when nutritionally complete diets are presented in open troughs to which birds have access. See Russell, H.G., "Blackbird Control at Two Army Installations: Environmental Impact Statement," Office Chief Eng., Directorate Facilities Eng., Washington D.C. (1975); Twedt D. J. and J. F. Glahn supra. (1092) and Rickaby, C. D., "A Review of the Nutritional Aspects of Complete Diets for Dairy Cows," *ADAS Q. Rev.*, 29:51–76 (1978). In such a situation, up to 9% of the high protein fraction of the diet can be eaten by birds, thus depriving livestock of a portion of their high value nutrient source and altering the composition of the entire ration. Feare, C. J. and J. T. Wadsworth, "Starling Damage on Farms Using the Complete Diet System of Feeding Dairy Cows," *Anim. Prod.* 32:179–183 (1981). Efforts to control problem birds at feedlots mainly have involved trapping and/or the use of lethal chemical agents. See Besser, J. F., W. C. Royall and J. W. DeGrazio supra. (1967); Bogadich, V., "The Use of Live Traps to Remove Starlings and Protect Agricultural Products," *Proc. Vertebr. Pest. Conf.* 3:98–99 (1968); Levingston, P. E., "Winter Starling Control with DRC-1339," *Proc. Vertebr. Pest. Conf.* 3:89–93 (1967); and Feare, C.J. and J.T. Wadsworth, supra. (1981). These approaches fail to create a sub-optimal environment for avian feeding activity, however, and the birds rapidly reinfest feedlots when control measures are relaxed. See Twedt, D. J. and J. F. Glahn, supra. (1982). Additional problems arise when lethal chemicals such as starlicide (1% C-cholor-p-toludine hydrochloride on poultry pellets) are used, including hazards to non-target animals, development of bait aversion by targeted birds, and increased expense and labor in prebaiting, baiting and monitoring. See Cummingham, D. J., E. W. Schafer and L. K. McConnell, "DRC-1339 and DRC-2698 Residues in Starlings: Preliminary Evaluation of Their Effects on Secondary Hazard Potential," *Proc. Bird Contr. Sem.* 8:31–37 (1979); and Glahn, J. F., "Use of Starlicide to Reduce Starling Damage at Livestock Feeding Operations," *Proc. Great Plains Wildl. Dam. Wrkshp.* 5:273–277 (1981). Twedt and Glahn outlined management practices that could be implemented at feedlots to substantially reduce bird depredation. Twedt, D. J. and J. F. Glahn, supra. (1982) Among the suggested practices was the use of feeds that are either unpalatable or that cannot be metabolized by birds. In the latter case, relatively high levels of non-protein nitrogen (e.g., urea) and/or alfalfa might be added. In the former case, certain tastants might be used. Compounds do exist that are unpalatable to birds but readily accepted by mammals. See Welty, J. C., "The Life of Birds" W. B. Saunders Book Co., Philadelphia, Pa., at page 72 (1975).

One compound found to be unpalatable to avian species is dimethyl anthranilate (DMA), a non-toxic food flavoring approved for human consumption but offensive to birds, even when presented at low concentrations. DMA has been suggested as a compound to reduce consumption of normally preferred foods by birds. See U.S. Pat. No. 2,967,128 (Kare).

In addition to the aforementioned losses of livestock feed and losses attributable to disease transmission caused by avian species, significant losses of crops and seeds can be attributed to consumption by such species. Crops which are susceptible to avian consumption include but are not limited to corn, rice, sorghum, grapes, cherries and blueberries.

In addition to the problems encountered in preventing loss of mammalian livestock feeds, crops and seeds to avian species, other problems result from the unwanted ingestion of materials intended for consumption by mammalian species. For example, pesticides such as herbicides, rodenticides and insecticides as well as fertilizers are often applied in pelletized form and persist in such form for long enough periods to be consumed in significant quantities by avian species. If the birds are not killed, they may concentrate lethal agents in such quantities as to cause the secondary poisoning of their predators. Since many of these predators are endangered species, a method of preventing avian prey from ingesting such substances should reduce the incidence of secondary poisonings. See Balcomb, R., "Secondary Poisoning of Red Shouldered Hawks With Carbonfuran:, *J. Wildl. Manage.* 47(4);1189–1132 (1983). Of course, consumption of the pesticides or fertilizers by avian species can also cause economic hardships to farmers in terms of crop loss and increased pesticide and fertilizer costs.

A primary object of this invention is the provision of a mammalian livestock feed which is not palatable to common avian species, such as starlings and blackbirds.

A further object of this invention is the provision of a method for reducing the amount of livestock feed lost to avian species.

A further object of this invention is the provision of an avian repellent composition which can be applied to crops and seeds to reduce avian consumption of such crops and seeds.

A further object of this invention is the provision of pesticidal and herbicidal compositions which are taste aversive to avian species.

These and other objects of the present invention will become apparent from the following description.

SUMMARY OF THE INVENTION

It has now been found that anthocyanin compounds are taste-repellent to many avian species, e.g., passerine species such as starlings and blackbirds. This invention therefore relates to methods of reducing the amounts of compositions lost to consumption by avian species comprising incorporating into or applying to said compositions an effective avian repellent amount of one or more anthocyanins or anthocyanin-containing plant species. The compositions intended for such use include any compositions which are susceptible to avian consumption, e.g., livestock feed, pelleted fertilizers and pesticides, crops and seeds.

This invention therefore more particularly relates to a novel mammalian livestock feed composition containing an amount of one or more anthocyanins or anthocyanin-containing plant species effective to at least significantly reduce the amount of feed consumed by avian species. This invention also relates to avan repellent compositions useful for applications to crops and seeds which compositions comprise inert ingredients and an amount of one or more anthocyanins effective to at least significantly reduce the amount of such crops and seeds consumed by avian species. Finally, this invention relates to pelleted pesticidal or fertilizer compositions which composition comprise a pesticide or fertilizer, an amount of one or more anthocyanins effective to at least significantly reduce the amount of pesticide or fertilizer composition consumed by avian species, and inert ingredients.

BRIEF DESCRIPTION OF THE DRAWINGS

The FIGURE is a graph presenting data comparing mean consumption by male starlings of distilled water versus distilled water containing 5% w/v enocyanin.

DETAILED DESCRIPTION OF THE INVENTION

Anthocyanins are flavinoid compounds widely distributed in nature. Present evidence indicated that they are harmless to human beings. Practically all vegetables, fruits, and processed foods and drinks based on plant materials (e.g., wine) contain these compounds, so that relatively large quantities are consumed daily. No deleterious effects have been associated so far with such ingestion (Harborne, Jeffrey, "Flavonoid Pigments," *Herbivores: Their Interaction With Secondary Plant Metabolites*, G. A. Rosenthal and D. H. Janzen (eds.), Academic Press: New York, C. 18, pp 619-655. Indeed, anthocyanins have commercial value as natural food dyes. Vacarri, A., P. G. Pifferi and G. Zaccerini, 1982, "Anthocyanins of Sunflower (*Helianthus annus*)," *J. Food Sci.*, 47:40-42. Nonetheless, it has now been discovered that anthocyanins (e.g., peonidin, cyanadin, delfinidin, and related anthocyanin derivatives) extracted from plant materials are repellent to many passerine species.

Anthocyanins are naturally occurring compounds which can be obtained by extraction from anthocyanin-containing plant species, e.g., by extraction of Neagra de Cluj (NdC) sunflower seeds with water or with methanol/hydrochloric acid mixtures. See Pifferi, P. G. and A. Vacarri, 1983, "The Anthocyanins of Sunflower" II A Study of the Extraction Process," *J. Food Technol.*, 18:629-638, the disclosure of which is hereby incorporated by reference. At least one anthocyanin, enocyanin, is commercially available. Tests indicate that anthocyanins obtained by extraction of NdC sunflower seeds with MeOH/HCl mixtures are more effective avian repellents than anthocyanins obtained by extraction of the same seeds with water. For such extractions, the volume percent of MeOH/HCl is generally in the range of about 99.6/0.4% to about 99.0/1.0%. The anthocyanins may be separated from the extract by means known in the art, e.g., by precipitation or evaporation.

The unique advantages of anthocyanins as avian repellents are threefold. First, they do not pose hazards to livestock or nontarget avian species. Second, because they may be applied directly to foodstuffs or crops, learned avoidance of treated materials may enhance efficacy. Finally, no effort in terms of prebaiting and monitoring is necessary, thus decreasing the costs of pest control.

The anthocyanins such as enocyanin and those obtained, for example, by extraction of sunflower seeds, are generally in powder form and can therefore simply be blended in powder or pelletized form in an effective avian-repellent amount (i.e., an amount to at least significantly reduce the amount of feed consumed by avian species) into a mammalian livestock feed. When incorporated in a feed, it is expected that the anthocyanins should comprise about 10% to 30%, preferably about 5.0% to 3.0% weight % of the livestock feed. Alternatively, anthocyanin-containing plant materials themselves, e.g., sunflower seeds, may be incorporated into the livestock feed.

By providing the aforementioned livestock feed, methods for reducing the loss of such feed to avian species and for facilitating the reduction of incidence of avian transmitted disease in mammalian livestock populations are provided.

Anthocyanins may also be blended in effective avian-repellent amounts with liquid or solid inert carriers or diluents to prepare avian repellent compositions suitable for application to crops and seeds. Suitable methods of formulation are well known to those skilled in the art. Solid formulations, for example, in the form of dusts or wettable powders, may be prepared by formulation with inert carriers or diluents such as clays or talc. Liquid formulations such as emulsions, emulsifiable concentrates, sprays and aerosols may be prepared by formulation of the anthocyanin with appropriate solvents, diluents and surface active agents. The anthocyanin may also be incorporated in other pesticidal or fungicidal compositions for application to crops or seeds.

By providing the aforementioned avian repellent compositions, methods for reducing the loss of crops and seeds caused by avian consumption are provided.

To reduce consumption of pelleted fertilizer and pesticide (e.g., insecticide, herbicide or rodenticide) compositions by gritting birds, effective avian-repellent amounts of anthocyanins may be incorporated in such pelleted fertilizer and pesticide compositions. The anthocyanins may be blended directly with the pesticide or fertilizer and the inert ingredients to form the pellet, or they may be dispersed in a liquid medium and sprayed onto such pellets.

By providing the aforementioned pelleted avian repellent fertilizer or pesticide compositions, a method for reducing the losses of pelleted fertilizer or pesticide compositions to avian consumption is provided.

Procedures used in discovering the repellent effects of anthocyanins are described below.

EXPERIMENT 1

Anthocyanins were extracted from NdC seed hulls by submerging the seeds either in water or in a solution of methanol (MeOH) and hydrochloric acid (1% HCl v/v). For the water extraction, the water was evaporated, leaving behind anthocyanin crystals. For the methanol extraction, the MeOH/HCl extracting solution was changed three times and extracts pooled. Dissolved anthocyanins in the samples were precipitated by adding a 1:1 mixture of hexane and diethyl ether.

Procedures as described above were used to obtain water extracts of J550 seeds, which do not contain anthocyanins. The extraction gave a tan powder of unknown composition. The yield was approximately 2.0%.

Ten red-winged blackbirds were selected as subjects. After adaptation to visual isolation, the birds were presented with purple distilled water as their only fluid source for 7 days. The shade of purple used matched the deep purple of the anthocyanin extract in aqueous solution. The colored water was presented to each bird in two calibrated 50 ml Richter tubes positioned 5 cm apart at the front of each cage. With the exception of drinking fonts which entered the cage, both tubes were concealed from the birds. Drinking during the first four hours of light was recorded, and the birds were assigned to groups on the basis of overall consumption.

On the eighth day and for six days thereafter, all birds were given two-tube preference tests during the first four hours of light. The experimental groups were given tests between varied concentrations of anthocyanin extract in one tube, and purple distilled water in the other. Over successive days, descending concentrations of extract were presented. Presentations were then repeated in an ascending series. Control groups were given tests between two tubes containing purple distilled water. The amount of fluid consumed for each tube was measured to the nearest ml on an hourly basis during the four hour test period. Positioning of the Richter tubes was counterbalanced over days so that each bird was presented with anthocyanin solution an equal number of times on the left and right sides of the cage. At the end of testing on each day, each bird was presented with two tubes of distilled water.

After anthocyanin tests, birds were adapted to drinking brown water from two Richter tubes and given preference tests between concentrations of J550 extract and brown distilled water. These tests were conducted in the same fashion as that described above.

The following table presents the mean consumption data in the two-choice drinking tests of (1) the water-extracted anthocyanin from hulls of NdC seeds, (2) the MeOH/HCl-extracted anthocyanin from hulls of NdC seeds and (3) the water-extracted material from hulls of J550 seeds. The standard error of the mean ranged from 0.3 to 4.4 for the means presented.

TABLE

Mean Consumption (ml) by Red-Winged Blackbirds in Two-Choice Drinking Tests

| % Conc. | $H_2O$ Extracted Anthocyanin (NdC) | Distilled $H_2O$ | MeOH/HCl Extracted Anthocyanin (NdC) | Distilled $H_2O$ | $H_2O$ Extracted Material (J550) | Distilled $H_2O$ |
|---|---|---|---|---|---|---|
| 2.5 | 5.1a | 16.1b | 1.5a | 10.4b | 0.9a | 13.4b |
| 2.0 | 5.8a | 17.4b | 2.7a | 13.6b | 3.1a | 11.5b |
| 1.5 | 6.8a | 16.3b | 3.7a | 12.2b | 3.2a | 14.0b |
| 1.0 | 8.3a | 14.6b | 5.1a | 13.5b | 8.7a | 9.1a |
| 0.5 | 7.8a | 12.1a | 6.1a | 13.5b | 5.7a | 8.2a |
| 0.0 | 11.4a | 8.1a | 4.6a | 9.5a | 8.2a | 4.8a |

The data in the foregoing table indicate that there were significant differences (ps 0.01) in repellent effects among varying anthocyanin concentrations; however, all concentrations were avoided relative to consumption of distilled water. Solutions of water extracts of J550 were also avoided, but avoidance of NdC extracts was relatively stronger and persisted at lower concentrations. MeOH/HCl extracts of NdC were avoided at lower concentrations than water extracts, and within two-choice test at each concentration, less MeOH/HCl extract was consumed than water extract (P 0.05).

EXPERIMENT II

A two-choice test similar to that described above in Experiment I was run except that male starlings were used as subjects, the birds were presented with stimuli 24 hours per day, and the commercially available anthocyanin, enocyanin, was used rather than extracts from NdC seeds. The FIGURE is a graph comparing the mean composition by the starlings of distilled water versus distilled water containing 5% w/v enocyanin. Each measurement interval ($T_1, T_2$, etc.) is a fifteen hour period. The points at $T_1$ and $T_2$ represent distilled water baseline consumption. Enocyanin was placed in one tube at intervals $T_3$–$T_5$. At each of measurement intervals $T_3$–$T_5$ enocyanin was strongly avoided. (ps 0.001).

What is claimed is:

1. A method for reducing the amount of a composition lost to avian consumption comprising incorporating into or applying to said composition an effective avian repellent amount of one or more anthocyanins.

2. A method of claim 1 where said anthocyanin is enocyanin.

3. A method of claim 1 where said anthocyanin is extracted from Neagra de Cluj sunflower seeds.

4. A method of claim 3 where said anthocyanin is extracted by a mixture of methanol and hydrochloric acid.

5. A mammalian livestock feed comprising:
   (a) a food component, and
   (b) an effective avian-repellent amount of one or more anthocyanins or anthocyanin-containing plant materials.

6. A feed according to claim 5 where said anthocyanin is enocyanin.

7. A feed according to claim 5 where said anthocyanin is extracted from Neagra de Cluj sunflower seeds.

8. A feed according to claim 7 where said anthocyanin is extracted by a mixture of methanol and hydrochloric acid.

9. A feed according to claim 5 in which the one or more anthocyanins is in the range of about 5% to 3% weight % of the feed.

10. A method of reducing the amount of mammalian livestock feed lost to consumption by avian species comprising incorporating into said feed an effective avian-repellent amount one or of more anthocyanins.

11. A method according to claim 10 where said anthocyanin is enocyanin.

12. A method according to claim 10 where said anthocyanin is extracted from Neagra de Cluj sunflower seeds.

13. A method according to claim 12 where said anthocyanin is extracted by a mixture of methanol and hydrochloric acid.

14. A method according to claim 13 where the amount of said one or more anthocyanins incorporated into said feed is in the range of about 5% to 3% weight % of the feed.

15. An avian repellent composition comprising an effective avian-repellent amount of one or more anthocyanin compounds and one or more liquid or solid carriers or diluents.

16. A method of reducing the amount of seeds or crops lost to consumption by avian species comprising applying to said seeds or crops an effective avian-repellent amount of one or more anthocyanins.

17. A pelleted pesticide or fertilizer composition comprising a pesticide or fertilizer, an effective avian-repellent amount of one or more anthocyanins and inert carriers or diluents.

18. A method of reducing the amount of pelleted pesticide or fertilizer compositions lost to consumption by avian species comprising incorporating into said pelleted pesticide or fertilizer an effective avian repellent amount of one or more anthocyanins.

19. A method of preparing an avian-repellent mammalian livestock feed comprising:
   (a) preparing an extract solution by submerging hulls of NdC sunflower seeds in a solution of methyl alcohol and hydrochloric acid;
   (b) separating anthocyanins from said extract solution, and
   (c) incorporating said anthocyanins in an effective avian-repellent amount in a mammalian livestock feed.

* * * * *